United States Patent [19]

Tremmel et al.

[11] 4,089,754
[45] May 16, 1978

[54] ELECTRODEPOSITION OF NICKEL-IRON ALLOYS

[75] Inventors: Robert Arnold Tremmel, Woodhaven; Roy Wilbur Herr, Troy, both of Mich.

[73] Assignee: Oxy Metal Industries Corporation, Warren, Mich.

[21] Appl. No.: 816,247

[22] Filed: Jul. 18, 1977

[51] Int. Cl.$^2$ ............................................. C25D 3/56
[52] U.S. Cl. .................................................. 204/43 T
[58] Field of Search ........................... 204/43 T, 48, 49

[56] References Cited

U.S. PATENT DOCUMENTS 3,878,067  4/1975  Tremmel ............................ 204/43 T Primary Examiner—G. L. Kaplan
Attorney, Agent, or Firm—B. F. Claeboe; Richard P. Mueller; Arthur E. Kluegel

[57] ABSTRACT

An aqueous bath suitable for the electrodeposition of a bright iron-nickel electrodeposit onto a substrate susceptible to corrosion comprising iron ions, nickel ions, a bath soluble primary nickel brightener containing a sulfo-oxygen group, a bath soluble complexing agent, and an auxiliary bath soluble nickel brightener containing a sulfo-oxygen group, said auxiliary brightener having the general formula:

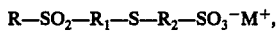

$$R-SO_2-R_1-S-R_2-SO_3^-M^+,$$

wherein
R is an aliphatic hydrocarbon moiety having 1 to 4 carbon atoms, or aryl,
$R_1$ and $R_2$ are aliphatic hydrocarbon moieties of from 1 to 4 carbon atoms,
R and $R_1$ may be linked together to form an organic radical when R is aliphatic, and
$M^+$ is hydrogen, sodium potassium, lithium or ammonium.

8 Claims, No Drawings

ELECTRODEPOSITION OF NICKEL-IRON ALLOYS

BACKGROUND OF THE INVENTION

It is known in the art to which this invention pertains to provide a nickel-iron electroplating bath which comprises a source of nickel ions provided by nickel sulfate and/or nickel chloride; a source of iron ions preferably in the form of ferrous sulfate; a complexing agent which again may be provided by a number of different compounds; boric acid; and a brightener of which again there are many types known to the art. Experience has indicated, however, that while this general formula offers many advantages over simple electrodeposited nickel-like coatings, primarily by way of corrosion resistance to metallic surfaces, it does upon occasion suffer from at least three disadvantages. The first, by reason of the presence of complexing and brightening agents, there may be an excessive amount of organic breakdown which tends to detract from the appearance of the deposit and may cause degeneration of its physical properties. There may also be present in the bath foreign organic materials which apparently are introduced therein inadvertently from a source such as cutting oils. A second problem with the general bath composition just mentioned is the presence in the bath of zinc and copper impurities. These may come from, among other sources, the workpieces being processed, such as brass parts. A third disadvantage of the general formula stated is that when the nickel-iron alloy has an iron content of about thirty-five percent (35%) or above, there arises rather critical parameters, and bath control is quite difficult.

It has been proposed by the prior art to endeavor to overcome the organic breakdown problem by treating the solution with a material such as activated carbon, however, this is a time-consuming and a relatively expensive procedure. With regard to the problem of the presence of zinc and copper deposits, it is known to use electrolytic purification, that is, to electrolyze the solution for rather extended periods of time at very low current densities. Again, this procedure is relatively time-consuming and costly. When working with nickel-iron alloys with an iron content at or above thirty-five percent (35%) and metallic impurities being present, there has not been found in the prior art literature a completely successful formulation which results in a deposit which possesses overall brightness and ductility, satisfactory plating in the recess areas, and optimum leveling.

SUMMARY OF THE INVENTION

It has now been discovered that each of the mentioned disadvantages of prior art nickel-iron bath compositions can be eliminated by the addition to a conventional bath comprising agents of what is referred herein as an auxiliary bath soluble brightener containing a sulfo-oxygen group, this novel auxiliary brightener having the general formula:

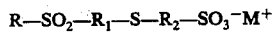

wherein

R is an aliphatic hydrocarbon moiety having 1 to 4 carbon atoms, or aryl, $R_1$ and $R_2$ are aliphatic hydrocarbon moieties of from 1 to 4 carbon atoms, R and $R_1$ may be linked together to form an organic radical when R is aliphatic, and $M^+$ is hydrogen, sodium, potassium, lithium or ammonium.

To be more specific, the novel auxiliary brightener of this invention is a sulfolane, which may take the form of sulfolane −3 thiopropane sulfonic acid, although as the description proceeds, variations from this particular compound are manifest and are within the purview of this invention. In any event, by this invention there is obtained a nickel-iron deposit having markedly improved brightness and good ductility. The novel plating solutions of this invention have thus essentially entirely eliminated the harmful effects caused primarily by excessive amounts of iron, zinc, and/or organic impurities.

DESCRIPTION OF PREFERRED EMBODIMENT

Applicants' invention is directed to the electrodeposition of a bright iron-nickel alloy deposit of from 5 to 50 percent by weight iron, preferably about 15 to about 35% by weight iron, which can be used as the basis for subsequent electrodeposition of chromium in order to impart desirable decorative and/or corrosion resistant properties to substrates, such as metallic substrates.

The bath and process of the present invention can also be used in the electrodeposition of nickel-iron alloy upon plastics. Normally the plastic substrate is acrylonitrilebutadiene-styrene, polyethylene, polypropylene, polyvinyl chloride, or phenol-formaldehyde polymers which are pretreated by applying a conductive metallic deposit such as nickel or copper onto the plastic substrate. The iron-nickel deposit may then be used as a subsequent coating onto the conductive metallic deposit.

The bath that may be employed in the present invention utilizes one or more salts of nickel, one or more salts of iron, a bath soluble primary nickel brightener containing a sulfo-oxygen group, a bath soluble complexing agent, and an auxiliary bath soluble nickel brightener containing a sulfo-oxygen group, the auxiliary brightener of this invention having the general formula:

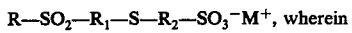

R is an aliphatic hydrocarbon moiety having 1 to 4 carbon atoms, or aryl, $R_1$ and $R_2$ are aliphatic hydrocarbon moieties of from 1 to 4 carbon atoms, R and $R_1$ my be linked together to form an organic radical when R is aliphatic, and $M^+$ is hydrogen, sodium, potassium lithium or ammonium.

In order to introduce iron and nickel ions into the bath, any bath soluble iron or nickel containing compound may be employed, providing the corresponding anion is not detrimental to the bath. Preferably inorganic nickel salts are employed, such as, nickel sulfate, nickel chloride, and the like as well as other nickel materials such as nickel sulfamate and the like. When nickel sulfate salts are used they are normally present in amounts ranging from about 40 to 300 grams/liter (calculated as nickel sulfate 6H₂O), although nickel chloride may also be used, and is then present in an amount ranging from about 80 to 250 grams/liter. The chloride or halide ions are employed in order to obtain satisfactory conductivity of the solution and at the same time to obtain satisfactory corrosion properties of the soluble anodes.

Preferably, the inorganic salts of iron are employed, such as, ferrous sulfate, ferrous chloride, and the like. These salts are generally present in an amount ranging from about 3 to 60 grams/liter. Other bath soluble iron salts may also be employed, as exemplified by soluble ferrous fluoborate, or sulfamate, and the like. The bath should contain not less than about 10 grams/liter of nickel plus ferric and ferrous ions.

The iron complexing agent employed in the instant invention is naturally bath soluble and is selected from the group consisting of carboxy and hydroxy groups, provided that at least one of the complexing groups is a carboxy group and also that there be at least two complexing groups present. The complexing agent that may be employed is present in an amount ranging from about 10 to about 100 grams/liter. Suitable complexing agents are hydroxy substituted lower aliphatic carboxylic acids having from 2 to 8 carbon atoms, from 1 to 6 hydroxyl groups and from 1 to 3 carboxyl groups such as citric acid, malic acid, gluteric acid, gluconic acid, muconic, glutamic, glucoheptonate, glycollic acid, aspartic acid, tartaric acid and the like, either used alone or in a combination with reducing agents such as dextrose, lactose and like compounds. As well, amine containing complexing agents, such as nitrilotriacetic acid, ethylenediamine tetra-acetic acid, and the water soluble salts thereof such as ammonium and the alkaline metal salts such as potassium, sodium, lithium and the like can be used. It will also be appreciated that the iron can be introduced into the bath as a salt of the complexing agent.

By "carboxy" is meant the group —COOH; however, the proton disassociates from the carboxy group in solution, and accordingly, this is intended to be included in the meaning of carboxy.

The pH of the bath preferably ranges from about 2.5 to about 5.5, and even more preferably from about 3.0 to 3.5. The temperature of the bath is desirably maintained from about 120° to about 180° F, and preferably the bath temperature is approximately 145° F.

The average cathode current density may range from about 25 amps to approximately 75 amps per square foot and preferably is about 40 amps per square foot.

It is preferred that the complexing agent concentration be at least three times the total iron ion concentration in the bath. The complexing agent concentration ratio to total iron ion may range from about 3:1 to 50:1.

While the bath may be operated without agitation, various means of agitation may be employed such as mechanical agitation, air agitation, cathode rod movement and the like.

Essentially, any bath soluble primary nickel brightening agents containing a sulfo-oxygen group may be utilized in order to impart brightness, ductility and leveling in the iron-nickel deposits. To enumerate, the brightening agents may be sulfo-oxygen compounds, acetylenic nickel brighteners, organic sulfides of the type described in U.S. Pat. No. 3,806,429 or similar materials. Naturally, these brighteners should be soluble in the electroplating bath.

The above described nickel-iron electroplating solution when formulated with particular ranges of nickel to iron ions and incorporating specific amounts of defined brightening and complexing agents, and further, when known parameters of pH, current density, bath temperature and other factors are observed, a nickel-iron deposit is obtained having a superior corrosion resistance and a brightness, ductility and leveling not heretofor acheived by prior art practices. However, even when operating under what appeared to be the mentioned optimum bath conditions there arises problems attributable in general to excessive amounts of iron, zinc and/or organic impurities. The specific problems created by the presence of these deleterious substances and the attempt made by the prior art to overcome them have been discussed hereinabove. In general, the remedies suggested have been far from completely successful. Applicants, on the other hand, have discovered that when under the general conditions noted there is added to a nickel-iron electroplating solution comprised of iron and nickel ions, a bath soluble primary nickel brightener and a bath soluble complexing agent, an auxiliary bath soluble nickel brightener of the character generally typified as thiosulfolanes the problems heretofor discussed are surprisingly effectively, and completely overcome.

Sulfolanes generally are of course well known to the art and are derived by the reaction of sulfur dioxide with butadiene to form sulfolene, which is then hydrogenated. A typical reaction involving the hydrogenation of 3-sulfolene is as follows:

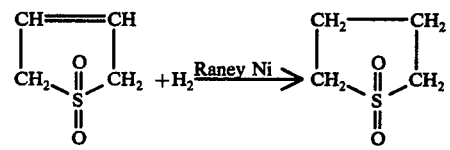

Sulfolane is a low melting, high boiling solid of exceptional thermal stability. It is a solvent for most organic compounds with the exceptions of parafins and cyaloalkanes, and for most polymers with the exceptions of polymethacrylates and polystyrene, and is miscible in water.

In the examples now to follow, test data will be presented utilizing exemplary nickel-iron bath formulation having substantially the composition set forth in Table A.

It is to be appreciated that various other additives may be employed to effect desirable results such as, surface active agents to overcome any undesirable problems that may occur in particular situations such as pitting.

When significant amounts of iron are being introduced into the system, it has been found that soluble iron anodes or nickel-iron alloy anodes should be employed. The ratio of nickel to iron in the anode area should be maintained at approximately 4 to 1. Anode bags, filter bags, hoses and tank linings should be those which are generally employed in other bright nickel processes.

EXAMPLE I

A commercial nickel-iron plating solution, constituted essentially as set forth in Table A, but containing a high concentration of iron in the general range of 40 to 45% and a high amount of organic degradation products, was plated in a 600 cc. air agitated cell. The operating pH of the bath was about 3.8 and the temperature was 140° F. A 1½ by 6 inches rolled steel panel was plated in the solution at 2 ASF for 15 minutes, and the resulting deposit was overall gray-white and blotchy, extremely stressed and brittle. The deposit had little brightness and leveling.

TABLE A

| Material | Concentration Range | Preferred Concenration |
| --- | --- | --- |
| Nickel sulfate | 40 to 300 grams/liter | 100 grams/liter |
| Nickel chloride | 50 to 250 grams/liter | 75 grams/liter |
| Ferrous sulfate | 5 to 40 grams/liter | 15 grams/liter |
| Complexing agent | 10 to 100 grams/liter | 20 grams/liter |
| Boric acid | 30 to 60 grams/liter | 45 grams/liter |
| Cathode current density average | 25 to 75 amps. sq. ft. | |
| Anode current density | 10 to 25 ASF | |
| Temperature | 110° F to 160° F | |
| pH | 2.5 to 5.5 | 3.0–4.2 |
| Agitation | air or rod | |
| Brightener | See above | |

EXAMPLE II

To a fresh sample of solution, there was added a compound having the following structure:

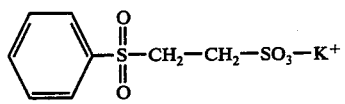

Panels were plated at a concentration range of 10 to 50 mg/l. No improvement in the deposit was observed.

EXAMPLE III

To another fresh sample of the test solution, there was added 15 mg/l of a compound having the structure immediately below:

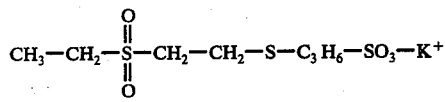

The subsequent panels were now overall bright, ductile, with good recess areas and leveling. Chrome coverage tests indicated that this compound does not appreciably reduce chrome receptivity at concentrations up to 30 mg/l.

EXAMPLE IV

Another fresh sample of the test solution was placed in an air agitated plating cell, and there was added to that a compound of this structure:

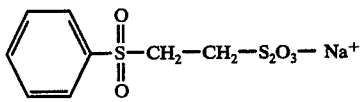

Initially 15 mg/l of this component was added, and although some improvement was noted, the deposit still was somewhat blotchy and brittle. Increasing the concentration to 30 mg/l produced a uniformly, lustrous deposit which had fairly good ductility, but virtually no leveling. Chrome coverage tests at this point indicated that the chromium receptivity was severely reduced.

EXAMPLE V

A commercial nickel-iron bath, constituted substantially as in Table A above, but contaminated with a large amount of degradation material was panel tested. The resulting deposit, which was plated on a 1½ by 6 inches bent steel cathode, was bright with non-uniform gray-white blotchy areas, and had poor ductility and leveling. 15 mg/l of sulfolane 3-thio propanesulfonate was added, and now the subsequent panel was overall bright, ductile and had very good leveling.

EXAMPLE VI

To another sample of the same solution, there was added 15 mg/l of thio dipropane sulfonic acid. Subsequent panel tests indicated that some of the blotchiness had been removed and there was an improvement in ductility, however, the leveling was still not very good. An additional 15 mg/l of the same compound produced an overall bright ductile deposit with poor leveling. Further tests were made on the solutions of both Example V and the present example to determine chromium receptivity. Results indicated that sulfolane 3-thio propane sulfonate markedly improved chrome coverage, while the compound of the instant example severely reduced chrome coverage.

EXAMPLE VII

A commercial nickel-iron plating bath, containing a high concentration of iron in the range of 40 to 45% and contaminated with a high amount of organic degradation material was placed in an air agitated plating cell. A 1½ by 6 inches rolled steel cathode was plated in the solution. The resulting deposit was overall gray-white and blotchy, extremely brittle, and had poor adhesion. Thereafter to a fresh sample of the above described solution there was added 15 mg/l of a compound having the following structure:

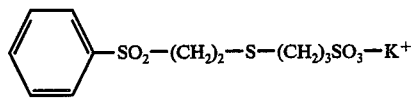

On the plated panel the resulting deposit was overall bright with good leveling, was quite ductile, and there was only a trace of poor adhesion. Chrome coverage tests indicated that this material had no adverse effect on chrome coverage at the above concentration.

EXAMPLE VIII

Again with the same test solution as described above, 15 mg/l of sulfolane 3-thio propionic acid was added and a rolled steel panel plated at 30 ASF for 15 minutes. The resulting deposit was improved, but still had a substantial amount of non-uniform gray-white blotchiness and was quite brittle. The concentration of the above described additive was increased to 30 mg/l and the panel repeated. Now the deposit was overall bright, ductile, with good adhesion but had only fair leveling. Chrome coverage tests at this point indicated that this material noticeably reduced chrome receptivity.

EXAMPLE IX

A commercial nickel-iron plating bath which was contaminated with organic and metallic impurities, the specific metallic contamination being about 100 mg/l of zinc, was tested in a 600 cc. air agitated plating cell. A rolled 1½ by 6 inches steel panel was plated in the solution at 40 ASF for 10 minutes, and the resulting deposit was overall gray and blotchy with dark striations in the low and intermediate current densities. 15 mg/l of sulfolane thio salycylic acid was added to a fresh sample of the above described solution and the panel was repeated. Little improvement was observed. The concentration was increased to 30 mg/l and the panel test repeated. The deposit was overall bright and had good leveling. However, subsequent chrome coverage tests indicated that the material caused a severe loss of chrome receptivity.

The entire test of this example was repeated using 15 mg/l of sulfolane 3-thio propane sulfonate, and an exceptable deposit was obtained with no adverse effects in chrome coverage.

EXAMPLE X

A commercial nickel-iron plating solution which was severely contaminated with organic breakdown material was set up in a 600 cc. air agitated plating cell. A rolled steel panel was plated at 45 ASF for 10 minutes. The resulting deposit was gray, blotchy with poor adhesion and low current density striations, and poor leveling.

10 mg/l of sulfolane 3-thio propane sulfonate was added and the panel repeated. The resulting deposit was overall bright and leveled, with a gray-white cloud in the intermediate currenty density area of the panel. The concentration of the sulfolane derivative was then increased to 20 mg/l and now the subsequent panel was overall bright, leveled, with a good recess and excellent adhesion.

EXAMPLE XI

A typical nickel-iron plating solution, constituted substantially as set forth in Table A above, was contaminated by the addition of 175 mg/l of zinc. Panel tests were made using rolled steel panels plated at 30 ASF for 10 minutes. The resulting deposits were bright, ductile, but were severely striated black in the low current density and intermediate current density areas.

However, the addition of 10 mg/l of sulfolane 3-thio propane sulfonate noticeably reduced the striations. 20 mg/l further improved the deposit. Chrome coverage tests were made and the results indicated about a 5% loss of chrome coverage at 20 mg/l concentration. At this point the tests were repeated on a fresh sample of the above described solution, however, in this experiment in addition to 20 mg/l of propane sulfonate, 150 mg/l of $CoSO_4 \cdot 6H_2O$ was added. Subsequent panels were overall bright, leveled, with excellent recess areas, and the chrome coverage was noticeably improved.

EXAMPLE XII

A commercial nickel-iron bath was utilized having the following concentrations of nickel and iron:

| | |
|---|---|
| $Ni^{+2}$ | 70.0 g/l |
| $Fe^{Total}$ | 11.65 g/l |
| $Fe^{+2}$ | 10.60 g/l |

Two amp. Hull Cell panels plated from this bath were cloudy bright from 0–10 ASF, bright from 70 to 100 + ASF, and gray black and brittle from 10 to 70 ASF, the latter being the normal plating range. Carbon treating this bath and adding back normal commercial brighteners failed to correct this problem for the reason that the deposit contained a very high iron concentration.

EXAMPLE XIII

An additive was made up having the following composition:

| | |
|---|---|
| Sulfolane 3-thio propane sulfonate | 8 g/l |
| Glyoxal bisulfite | 12 g/l |
| Cobalt sulfate | 100 g/l |

One cc/l of this mixture was added to a fresh sample of the bath of Example XII, and the subsequent Hull Cell was overall bright across the entire panel.

An exemplary method of preparing sulfolanes by reacting sulfur dioxide with butadiene to form sulfolene, and then hydrogenating this compound, was set forth in an earlier portion of this specification. In a generally similar fashion the compounds of Examples III and XI above may be prepared by the addition of mercaptans by this general reaction:

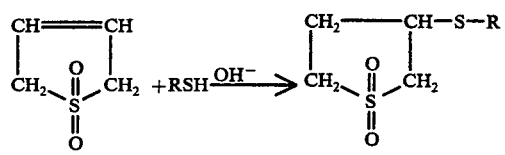

Hydrogen sulfide, primary, secondary and even tertiary mercaptans add to 3-sulfolene with ease. As is to be appreciated the above reaction is general for acylic α,β unsaturated sulfones as well.

It is believed readily apparent from the foregoing that by proceeding in accordance with the novel concepts of this invention there is essentially entirely eliminated in nickel-iron alloy plating solutions the deleterious effects of excessive amounts of organic breakdown, zinc impurities, and the difficulties caused when the iron alloy content is above about 35%. Quite clearly from a review of the disclosure presented various changes and modifications may be made in the bath compositions and method of electroplating without departing from the spirit of this invention or the scope of the subjoined claims.

We claim:

1. An aqueous acidic bath suitable for the electrodeposition of a bright iron-nickel electrodeposit onto a substrate susceptible to corrosion comprising iron ions, nickel ions, a bath soluble primary nickel brightener containing a sulfo-oxygen group, a bath soluble complexing agent, and an auxiliary bath soluble nickel brightener containing a sulfo-group, said auxiliary brightener having the general formula:

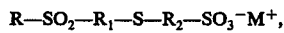

wherein
R is an aliphatic hydrocarbon moiety having 1 to 4 carbon atoms, or aryl,
$R_1$ and $R_2$ are aliphatic hydrocarbon moieties of from 1 to 4 carbon atoms,
R and $R_1$ may be linked together to form an organic radical when R is aliphatic, and
$M^+$ is hydrogen, sodium, potassium, lithium or ammonium.

2. An aqueous bath as defined in claim 1, in which the auxiliary brightener has the general formula:

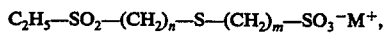

wherein $n$ = 1 to 4

$m$ = 1 to 4.

3. An aqueous bath as defined in claim 1, in which the auxiliary brightener has the general formula:

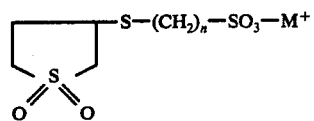

wherein $n$ = 1 to 4.

4. An aqueous bath as defined in claim 3, in which the general formula $n$ = 3.

5. An aqueous bath as defined in claim 1, in which there is also present a source of cobalt ions.

6. An aqueous bath as defined in claim 5, in which there is also present glyoxal bisulfite.

7. An aqueous bath as defined in claim 1, in which the ratio of nickel ions to iron ions is from about 5 to about 50 to 1, the bath soluble primary nickel brightener is present in an amount of about 0.5 to 10 g/l, the complexing agent is present in an amount of about 10 to about 100 g/l, and the auxiliary nickel brightener is present in an amount of about 1.0 to 100 mg/l.

8. A process for producing a bright iron-nickel alloy electrodeposit, which comprises passing a current through the bath of claim 1, and electrodepositing an iron-nickel alloy containing from about 5 to about 50% iron onto a cathodic surface.

* * * * *